(12) United States Patent
Pierce

(10) Patent No.: US 9,918,843 B2
(45) Date of Patent: Mar. 20, 2018

(54) SPECTRUM KNEE

(71) Applicant: Biomet Manufacturing, LLC, Warsaw, IN (US)

(72) Inventor: Andrew Pierce, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/174,106

(22) Filed: Feb. 6, 2014

(65) Prior Publication Data

US 2015/0216669 A1    Aug. 6, 2015

(51) Int. Cl.
*A61F 2/38*       (2006.01)
*A61F 2/30*       (2006.01)

(52) U.S. Cl.
CPC ............ *A61F 2/3859* (2013.01); *A61F 2/389* (2013.01); *A61F 2/3886* (2013.01); *A61F 2/30734* (2013.01); *A61F 2002/305* (2013.01); *A61F 2002/3037* (2013.01); *A61F 2002/30329* (2013.01); *A61F 2002/30332* (2013.01); *A61F 2002/30378* (2013.01); *A61F 2002/30433* (2013.01); *A61F 2002/30604* (2013.01); *A61F 2002/30607* (2013.01); *A61F 2002/30736* (2013.01); *A61F 2002/30878* (2013.01)

(58) Field of Classification Search
CPC ............ A61F 2/389; A61F 2002/30604; A61F 2/30734; A61F 2002/30329; A61F 2002/30736; A61F 2002/30332
USPC .......................................... 623/20.15, 20.32
See application file for complete search history.

(56) References Cited

U.S. PATENT DOCUMENTS

| | | | | |
|---|---|---|---|---|
| 5,263,987 | A * | 11/1993 | Shah | A61F 2/30721 606/86 R |
| 8,617,250 | B2 | 12/2013 | Metzger | |
| 2005/0154470 | A1* | 7/2005 | Sekel | A61F 2/389 623/20.15 |
| 2006/0004460 | A1* | 1/2006 | Engh | A61F 2/38 623/20.21 |
| 2006/0190086 | A1* | 8/2006 | Clemow | A61F 2/38 623/20.15 |
| 2006/0265079 | A1* | 11/2006 | D'Alessio, II | A61F 2/389 623/20.15 |
| 2007/0173858 | A1* | 7/2007 | Engh | A61F 2/38 606/99 |
| 2012/0101587 | A1* | 4/2012 | Forsell | A61F 2/3859 623/20.31 |
| 2012/0265317 | A1* | 10/2012 | Metzger | A61F 2/389 623/20.33 |

* cited by examiner

*Primary Examiner* — David H. Willse
*Assistant Examiner* — Javier Blanco
(74) *Attorney, Agent, or Firm* — Schwegman Lundberg & Woessner, P.A.

(57) ABSTRACT

A knee replacement system including a first tibial baseplate, a second tibial baseplate, and an intercondylar bridge member. Each one of the first and second tibial baseplates includes a bone engaging surface and a bearing engaging surface opposite to the bone engaging surface. Each one of the first and second tibial baseplates also includes a first baseplate coupling portion and a second baseplate coupling portion. The first baseplate coupling portion is configured to couple with the intercondylar bridge member for coupling the second tibial baseplate to the first tibial baseplate. The second baseplate coupling portion is configured to couple an insert to the first and second tibial baseplates.

8 Claims, 8 Drawing Sheets

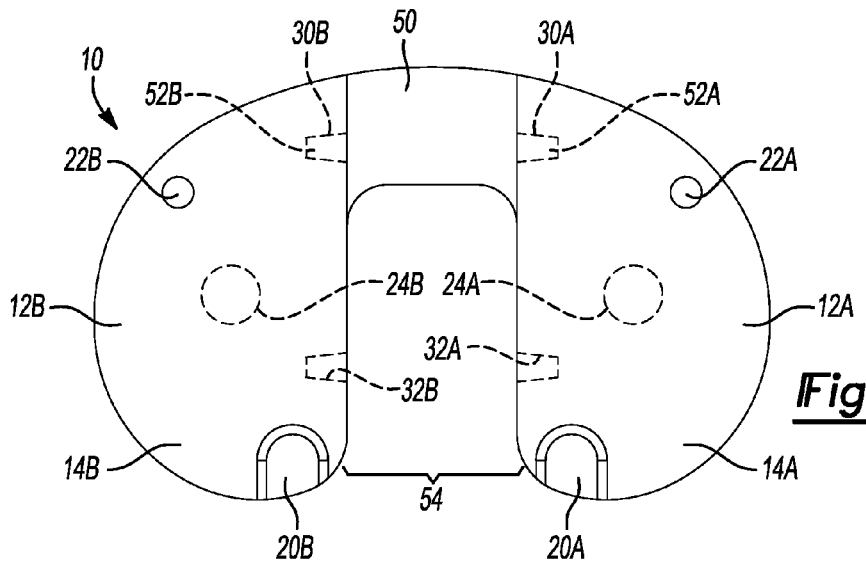
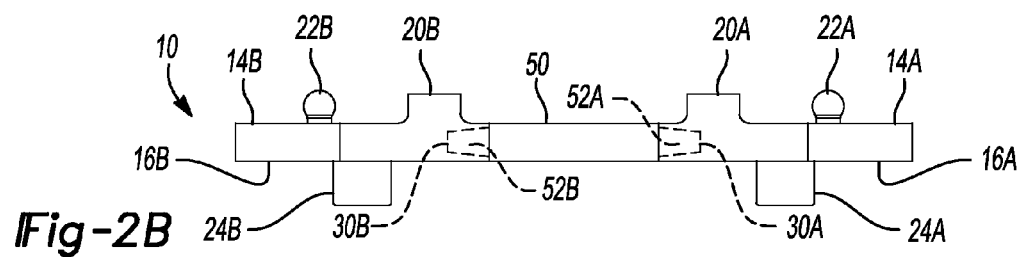
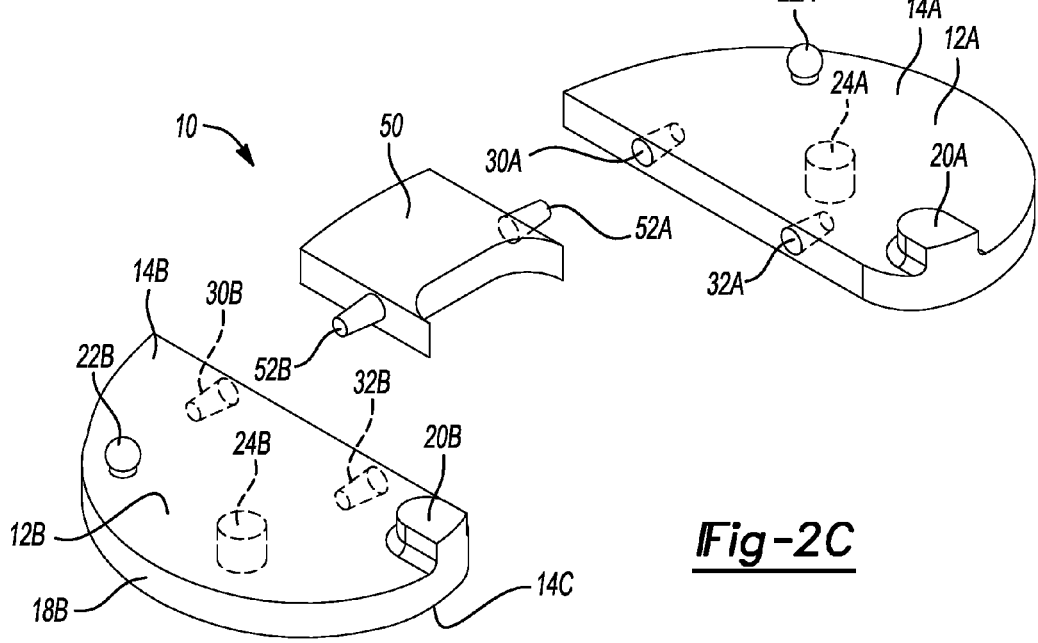

SPECTRUM KNEE

FIELD

The present disclosure relates to a knee replacement system for use with multiple types of arthroplasties, such as partial or salvage arthroplasties, for example.

BACKGROUND

This section provides background information related to the present disclosure which is not necessarily prior art.

Different types of knee arthroplasties can be performed based on the level of deterioration and/or damage to a knee. For each such arthroplasty, different instrumentation sets and implant components are typically required, each of which traditionally have few, if any, parts in common. For example, if the damage or deterioration is minimal, a partial replacement can be performed by implanting a medial or lateral condylar member in the femur, and a corresponding medial or lateral tibial component opposite thereto in the tibia. If both the medial and the lateral condyles are damaged or deteriorated and the level of knee constraint required is minimal, a cruciate retaining femoral component including medial and lateral condyles can be implanted in the femur, and a bi-cruciate tibial component including medial and lateral tibial baseplates and bearings can be implanted in the femur. If additional knee constraint is required, a posterior stabilized femoral component including an intercondylar box may be implanted. If additional stability on the tibia is appropriate, a tibial component including an intercondylar stem for implantation into the tibia can be used. Tibial and femoral components coupled together with a hinge therebetween can be used in some arthroplasties as well. In the case of a revision or salvage arthroplasty, tibial and femoral components including bone augments can be used to replace lost bone. A knee replacement system including a universal tibial component and a universal femoral component that can be modified for use in a plurality of different arthroplasties, such as from partial replacement through salvage, would thus be desirable

SUMMARY

This section provides a general summary of the disclosure, and is not a comprehensive disclosure of its full scope or all of its features.

The present teachings provide for a knee replacement system including a first tibial baseplate, a second tibial baseplate, and an intercondylar bridge member. Each one of the first and second tibial baseplates includes a bone engaging surface and a bearing engaging surface opposite to the bone engaging surface. Each one of the first and second tibial baseplates also includes a first baseplate coupling portion and a second baseplate coupling portion. The first baseplate coupling portion is configured to couple with the intercondylar bridge member for coupling the second tibial baseplate to the first tibial baseplate. The second baseplate coupling portion is configured to couple an insert to the first and second tibial baseplates.

The present teachings further provide for a knee replacement system including a femoral component. The femoral component includes: a medial condylar member including a medial coupling portion; a lateral condylar member including a lateral coupling portion; and a patellar member including a first coupling portion and a second coupling portion. The first coupling portion is configured to couple with the medial coupling portion to couple the medial condylar member and the patellar member together. The second coupling portion configured to couple with the lateral coupling portion to couple the lateral condylar member and the patellar member together.

The present teachings further provide for a knee replacement system including a tibial component and a femoral component. The tibial component includes a medial tibial baseplate and a lateral tibial baseplate, each of which include an anterior coupling portion and a posterior coupling portion. The tibial component also includes an intercondylar bridge member configured to couple the medial and the lateral tibial baseplates together so as to define a space therebetween. The intercondylar bridge member includes a first bridge coupling portion configured to couple with the anterior coupling portion of the medial tibial baseplate and a second bridge coupling portion configured to couple with the anterior coupling portion of the lateral tibial baseplate. The femoral component includes a patellar member including a first coupling portion and a second coupling portion. The femoral component also includes a medial condylar member including a medial coupling portion configured to couple with the first coupling portion, and a lateral condylar member including a lateral coupling portion configured to couple with the second coupling portion.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2A is a superior planar view of a tibial component according to the present teachings, the tibial component including the first or medial tibial baseplate and a second or lateral tibial baseplate coupled thereto with an intercondylar bridge member;

FIG. 2B is a posterior view of the tibial component of FIG. 2A;

FIG. 2C is a perspective view of the tibial component of FIG. 2A;

Corresponding reference numerals indicate corresponding parts throughout the several views of the drawings.

DETAILED DESCRIPTION

Example embodiments will now be described more fully with reference to the accompanying drawings.

Figure 1A:
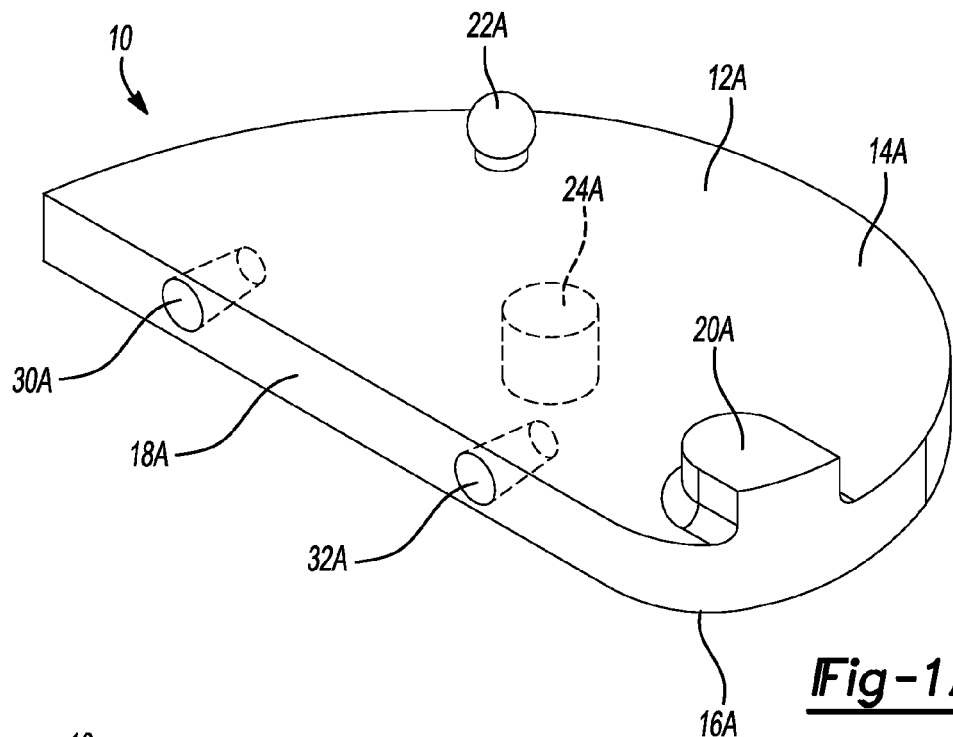
FIG. 1A is a perspective view of a first or medial tibial baseplate of a tibial component according to the present teachings.
Figure 1B:
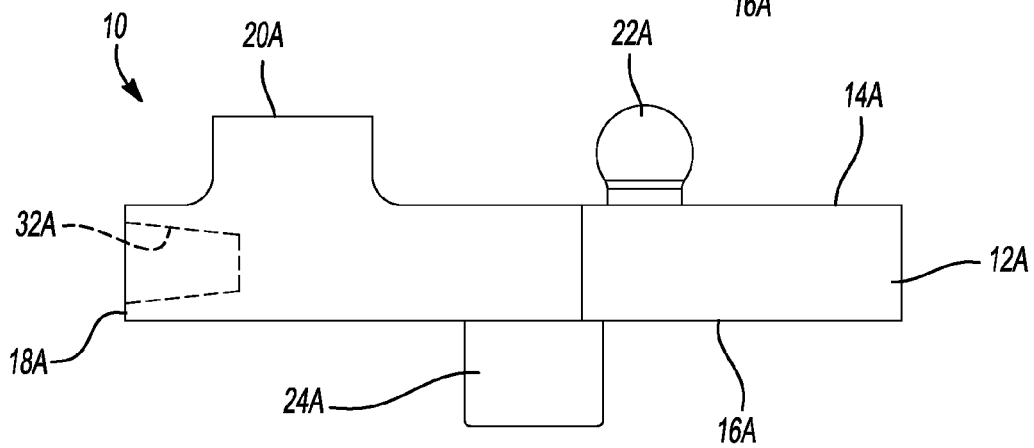
FIG. 1B is a posterior view of the first tibial baseplate of FIG. 1A.
Figure 1C:
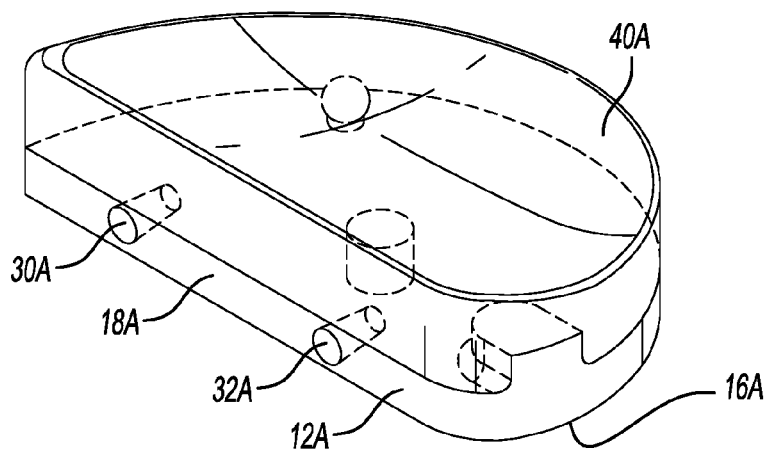
FIG. 1C illustrates a tibial bearing coupled to the first tibial baseplate.

With initial reference to FIGS. 1A, 1B, and 1C, a universal tibial component according to the present teachings is generally illustrated at reference numeral 10. The tibial component 10 described herein, along with a universal femoral component 210 described herein, provide components of a universal knee replacement system according to the present teachings. Various different tibial and femoral members described herein can be selectively coupled together to adapt the universal tibial component 10 and the universal femoral component 210 for use with various different arthroplasties, such as arthroplasties ranging from unicondylar replacement to salvage arthroplasties. Thus completely different femoral and tibial components need not be provided for each different arthroplasty, which conserves materials, costs, and storage space.

The first or medial tibial baseplate 12A generally includes a bearing engaging surface 14A and a bone engaging surface 16A opposite thereto. Between the bearing engaging surface 14A and the bone engaging surface 16A is a side surface 18A. At the bearing engaging surface 14A is a flange 20A and a post 22A extending therefrom. The flange 20A and the post 22A are configured to couple a tibial bearing 40A (FIG. 1C) to the medial tibial baseplate 12A. In addition to or in place of the flange 20A and the post 22A, any suitable coupling member configured to secure the bearing 40A to the bearing engaging surface 14A can be included. For example, any of the coupling members or features set forth in the following U.S. Patent may be used, which is incorporated herein by reference: U.S. Pat. No. 8,617,250 titled "Revision Knee Tibial Locking Mechanism" assigned to Biomet Manufacturing, LLC of Warsaw, Ind.

Extending from the bone engaging surface 16A is a bone anchor 24A. The bone anchor 24A is generally illustrated as a circular post, but can have any suitable size or shape suitable for anchoring the medial tibial baseplate 12A to a tibia bone. Although only a single bone anchor 24A is illustrated, any suitable number of bone anchors having any suitable size, shape, or configuration can be included at the bone engaging surface 16A to facilitate coupling of the medial tibial baseplate 12A to the tibia.

The side surface 18A includes an anterior baseplate coupling portion or member 30A and a posterior baseplate coupling portion or member 32A. As illustrated, the anterior baseplate coupling portion 30A and the posterior baseplate coupling portion 32A each are conical receptacles defined within the medial tibial baseplate 12A, which are tapered such that a largest diameter thereof is at the side surface 18A, and a smallest diameter thereof is furthest within the medial tibial baseplate 12A. The anterior and posterior baseplate coupling portions or members 30A and 32A are tapered to permit coupling with corresponding coupling portions or members as described herein, such as tapered posts sized and shaped to be received within the anterior and posterior baseplate coupling portions or members 30A and 32A, and retained therein with a taper lock, for example. In addition to the illustrated configuration, the anterior baseplate coupling portion or member 30A and the posterior baseplate coupling portion or member 32A can have any other suitable shape or configuration in order to couple the medial tibial baseplate 12A to other portions of the universal tibial component 10, as described herein.

With continued reference to FIGS. 1A-1C and additional reference to FIGS. 2A-2C, a second or medial tibial baseplate 12B according to the present teachings is illustrated. The tibial baseplate 12B is substantially similar or identical to the tibial baseplate 12A. Therefore, the description of the medial tibial baseplate 12A also applies to the lateral tibial baseplate 12B, and features of the lateral tibial baseplate 12B in common with the medial tibial baseplate 12A are illustrated with the same reference numbers, but include the suffix "B" rather than the suffix "A" used to designate the features of the medial tibial baseplate 12A.

The tibial component 10 further includes an intercondylar bridge member 50. The intercondylar bridge member 50 includes a first bridge coupling portion 52A and a second bridge coupling portion 52B. The first and second bridge coupling portions 52A and 52B are on opposite sides of the bridge member 50. The first bridge coupling portion 52A is configured to couple with the anterior baseplate coupling portion 30A of the medial tibial baseplate 12A. The second bridge coupling portion 52B is configured to couple with the anterior baseplate coupling portion 30B of the lateral tibial baseplate 12B. Thus the bridge member 50 can couple the medial and lateral tibial baseplates 12A and 12B together to provide a bi-cruciate tibial component 10 for implantation on a damaged tibia bone.

As illustrated, the first and second bridge coupling portions 52A and 52B are each conical posts extending from opposite sides of the bridge member 50. The first and second bridge coupling portions 52A and 52B are tapered such that they each have a largest diameter at the bridge member 50, and a smallest diameter most distal to the bridge member 50. However, the first and second bridge coupling portions 52A and 52B can each have any suitable size, shape or configuration in order to securely mate with the anterior baseplate coupling portions 30A and 30B of the medial and lateral tibial baseplates 12A and 12B respectively, such as with a taper lock for example.

Figure 3A:
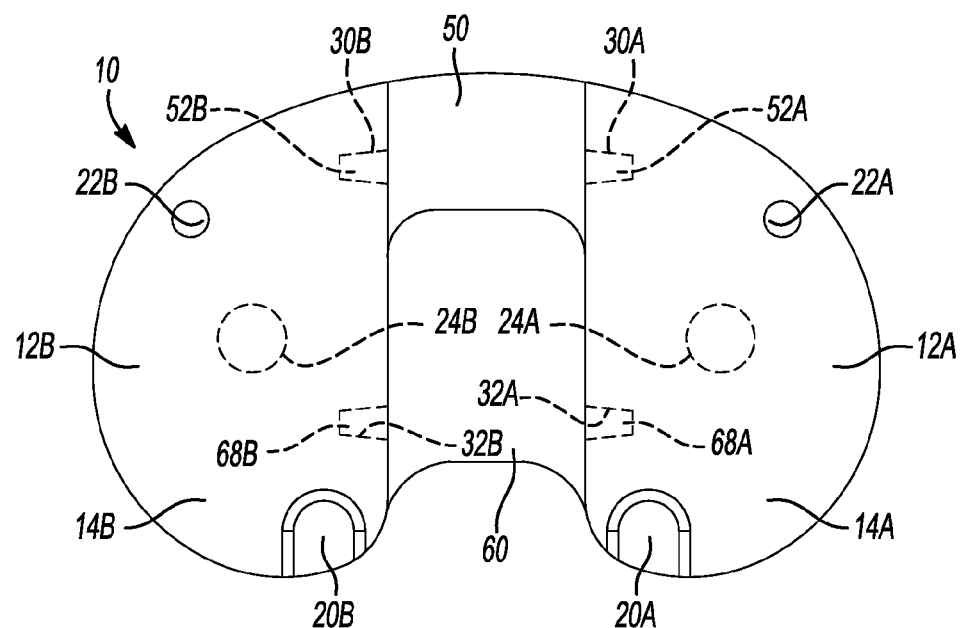
FIG. 3A is a superior planar view of the tibial component including an intercondylar insert mounted to and between the first and second tibial baseplates.
Figure 3B:
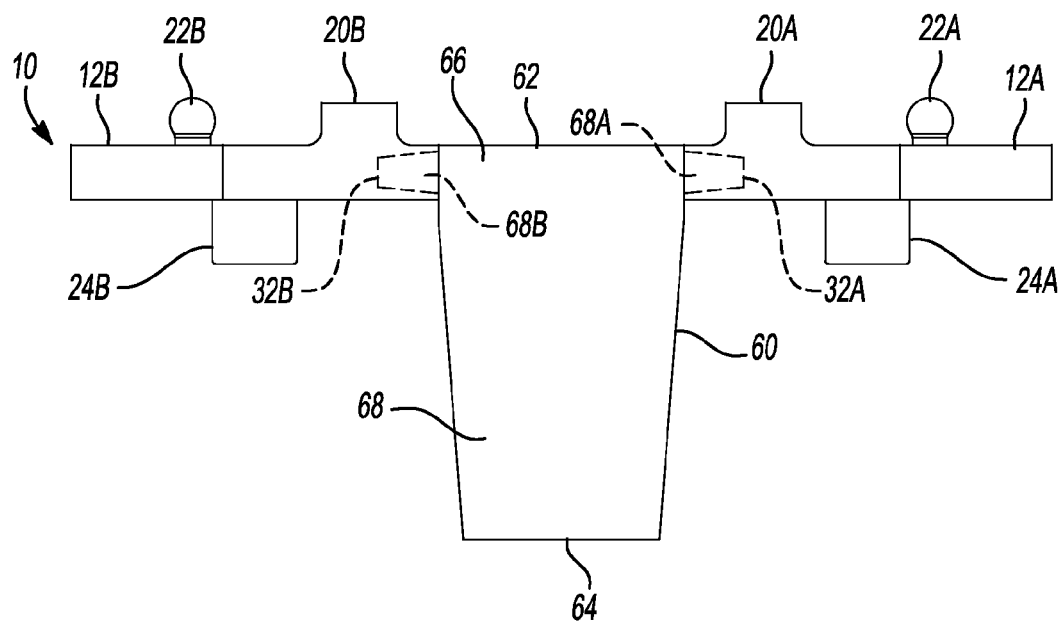
FIG. 3B is a posterior view of the tibial component of FIG. 3A.

With additional reference to FIGS. 3A and 3B, the tibial component 10 can further include an insert 60 coupled thereto. The insert 60 generally includes a superior end 62 and an inferior end 64, which is opposite to the superior end 62. At the superior end 62 is a base portion 66. Extending from the base portion 66 to the inferior end 64 is a stem 68. Extending from opposite sides of the insert 60 at the base portion 66 is a first insert coupling portion 68A and a second insert coupling portion 68B. The first inert coupling portion 68A is positioned, sized, and shaped to mate with the posterior baseplate coupling portion 32A of the medial tibial baseplate 12A. The second insert coupling portion 68B is positioned, sized, and shaped to mate with the posterior baseplate coupling portion 32B of the lateral tibial baseplate 12B. Thus the first and second insert coupling portions 68A and 68B are configured to couple the insert 60 to the medial and lateral tibial baseplates 12A and 12B within the space 54. Specifically and with reference to 3B, the base portion 66 is arranged in the space 54 such that the superior end 62 is generally coplanar with the bearing engaging surfaces 14A and 14B and the stem 68 extends beyond the bone engaging surfaces 16A and 16B. The stem 68 can be anchored within the tibia in any suitable manner, such as with bone cement, in order to enhance fixation of the tibial component 10 to the tibia. When provided with the insert 60, the universal tibial component 10 takes the form of a primary cruciate, full, or I-beam tibial component.

Figure 4A:
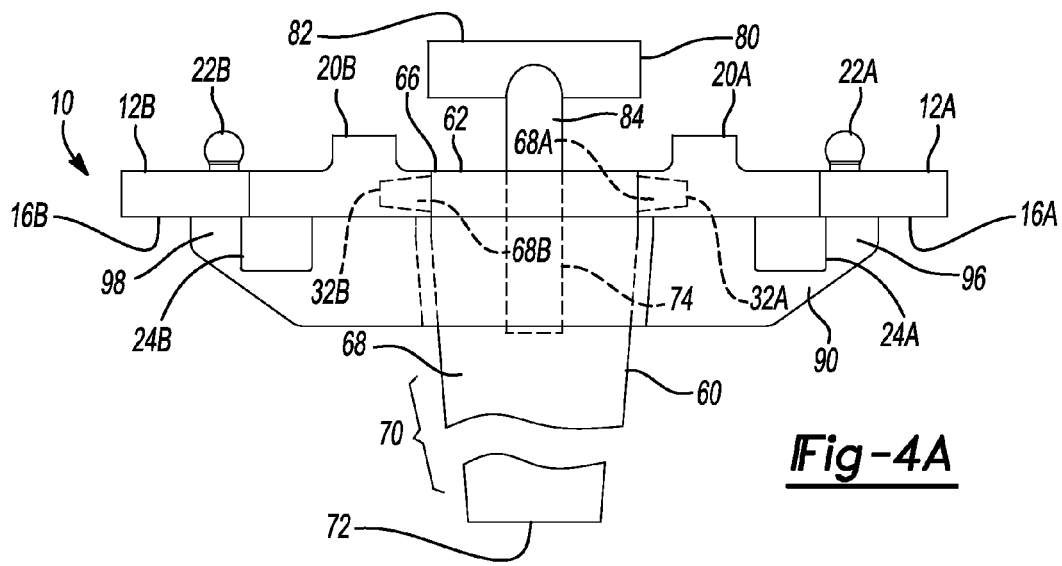
FIG. 4A is a posterior view of the tibial component including an insert with an elongated stem and a yoke seated in a receptacle thereof, and an augment mounted to the insert.
Figure 4B:
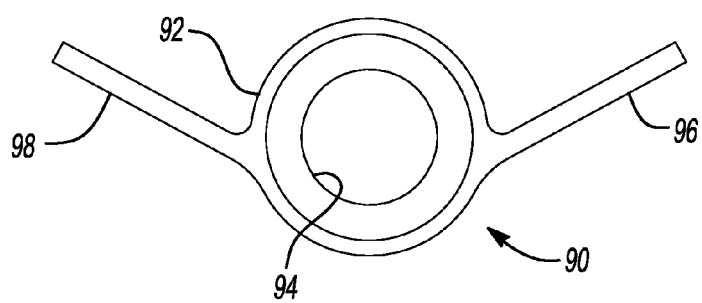
FIG. 4B is a planar view of the augment of FIG. 4A.

With additional reference to FIGS. 4A and 4B, the insert 60 can include an elongated stem 70, which is longer than the stem 68. The elongated stem 70 extends from the base portion 66 to an inferior end 72, which is further from the base portion 66 as compared to the inferior end 64 of the stem 68. The elongated stem 70 can be used when additional tibial fixation may be desirable, such as during a revision procedure. The knee replacement system according to the present teachings may thus include multiple inserts 60, such as an insert 60 including the stem 68, as well as an additional insert 60 including the elongated stem 70, each of which may be individually and selectively coupled to the medial and lateral tibial baseplates 12A and 12B as appropriate depending on the arthroplasty.

The insert 60 may also define a receptacle 74 extending into the insert 60 from the superior end 62, which defines an opening of the receptacle 74. The receptacle 74 can extend through the base portion 66 and into the elongated stem 70 as illustrated in FIG. 4A. The insert 60 of FIG. 3B including the stem 68 may include the receptacle 74 as well.

Figure 11:
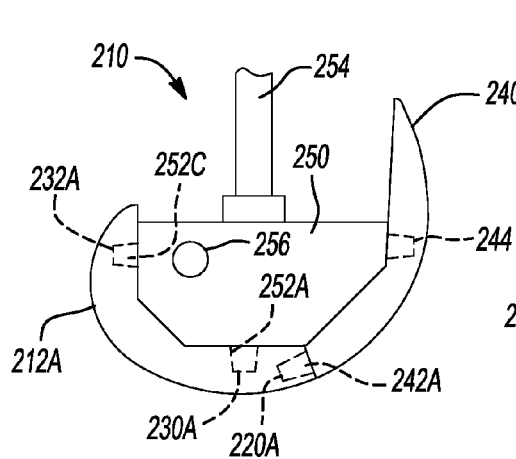
FIG. 11 is a side view of the femoral component according to the present teachings with the modular box further including a receptacle configured to receive the yoke to provide articulation between the femoral component and the tibial component.
Figure 12:
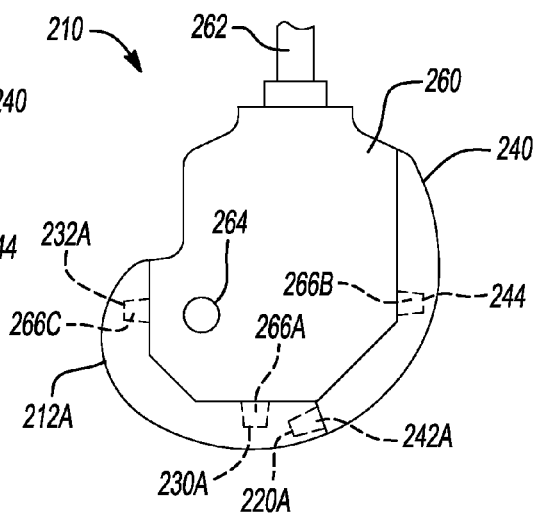
FIG. 12 is a side view of the femoral component according to the present teachings including a salvage bone augment defining a receptacle configured to receive the yoke.

The receptacle 74 is sized and shaped to receive a yoke 80 therein. The yoke 80 includes an articulation portion 82 and a stem 84 extending therefrom. The articulation portion 82 is arranged generally perpendicular to the stem 84. The stem 84 extends into the receptacle 74. In general, the stem 84 is not rigidly received in the receptacle 74, but rather slidably received therein to allow the yoke 80 to translate in an inferior and superior direction with the stem 84 slidably movable within the receptacle. The yoke 80 is configured to articulate with the femoral component 210 as described herein in order to provide the knee replacement system of the present teachings with a bone conserving hinge, as illustrated in FIG. 11 for example. The yoke 80 is also useful in salvage arthroplasties, such as those calling for use of a segmental implant, as illustrated in FIG. 12 for example.

The tibial component 10 can further include an augment 90, as illustrated in FIGS. 4A and 4B. The augment 90 can include a hub 92 with a first wing 96 and a second wing 98 extending therefrom. The hub 92 can be generally circular and can define a tapered coupling surface 94 therein. The first and second wings 96 and 98 can extend from the hub 92 in any suitable manner, such as linearly or at an angle as illustrated in FIG. 4B. The augment 90 can be coupled to the insert 60 by sliding the hub 92 over the stem 68 or the elongated stem 70, each of which are tapered in the direction of the inferior ends 64 and 72 respectively, in order to couple the hub 92 to the inserts 60 by way of a taper lock between the tapered coupling surface 94 of the augment 90 and the tapered stem 68 or the tapered elongated stem 70. The augment 90 can be positioned such that the first and second wings 96 and 98 are proximate to, or in contact with, the bone engaging surfaces 16A and 16B. Because the first and second wings 96 and 98 are arranged in parallel but offset planes, the first wing 96 can be arranged on an anterior side of a bone anchor 24A and the second wing 98 can be arranged on a posterior side of the bone anchor 24B. The augment 90 as illustrated in FIGS. 4A and 4B is generally configured as a fin augment suitable for accommodating and filling tibial bone loss.

Figure 5:
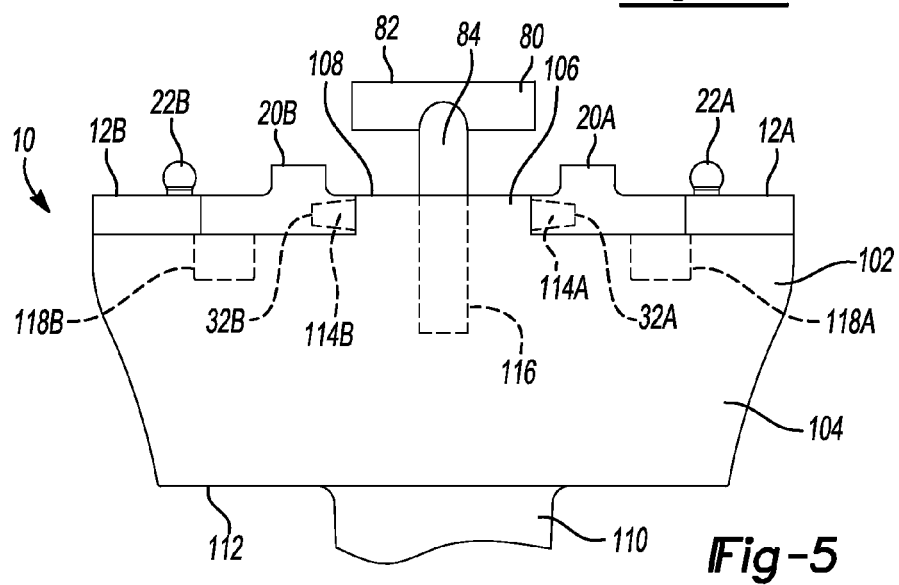
FIG. 5 illustrates the tibial component with another augment according to the present teachings mounted thereto.

With additional reference to FIG. 5, an additional augment according to the present teachings is illustrated at reference numeral 102. The augment 102 generally includes a body 104 and a base portion 106. The base portion 106 is at a superior end 108 of the augment 102. The body 104 extends from the base portion 106 to inferior end 112. The body 104 can have any suitable size, shape, or configuration to accommodate tibial bone loss, such as a generally cylindrical shape, or an enlarged (as compared to the augment 90 of FIGS. 4A and 4B) wing shape. Extending from opposite sides of the base portion 106 is a first augment coupling portion 114A and a second augment coupling portion 114B.

The first augment coupling portion 114A is positioned, sized, and shaped to cooperate with the posterior baseplate coupling portion 32A of the medial tibial baseplate 12A in order to couple the augment 102 to the medial tibial baseplate 12A. The second augment coupling portion 114B is positioned, sized, and shaped to cooperate with the posterior baseplate coupling portion 32B of the lateral tibial baseplate 12B in order to couple the augment 102 to the lateral tibial baseplate 12B. As illustrated, the first and second augment coupling portions 114A and 114B are each posts extending from opposite sides of the base portion 106. However, the first and second augment coupling portions 114A and 114B can be of any suitable size, shape or configuration, or any other suitable coupling member or device, configured to couple the augment 102 to the medial and lateral tibial baseplates 12A and 12B.

The augment 102 further includes a stem 110 extending from the inferior end 112 of the body 104. The stem 110 can have any length suitable to secure the augment 102, and the medial and lateral tibial baseplates 12A and 12B coupled thereto, to a tibia bone. The augment 102 further defines a receptacle 116 extending from the superior surface 108 through the base portion 106 and into the body 104. The receptacle 116 is similar to the receptacle 74, and is thus sized and shaped to slidably receive the stem 84 of the yoke 80 therein.

The augment 102 also includes a medial receptacle 118A and a lateral receptacle 118B. The medial and lateral receptacles 118A and 118B are generally cylindrical, and are sized, shaped, and positioned to respectively receive therein the bone anchor 24A of the medial tibial baseplate 12A and the bone anchor 24B of the lateral tibial baseplate 12B. The medial and lateral receptacles 118A and 118B thus serve to enhance coupling of the augment 102 to the medial and lateral tibial baseplates 12A and 12B.

Figure 6A:
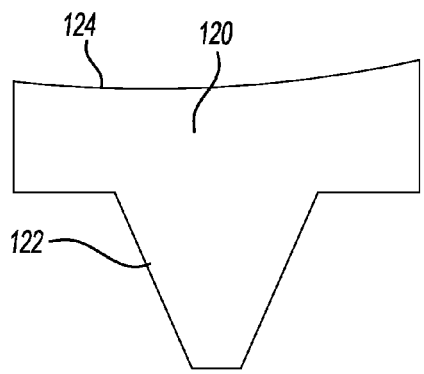
FIG. 6A illustrates a rotatable bearing according to the present teachings.
Figure 6B:
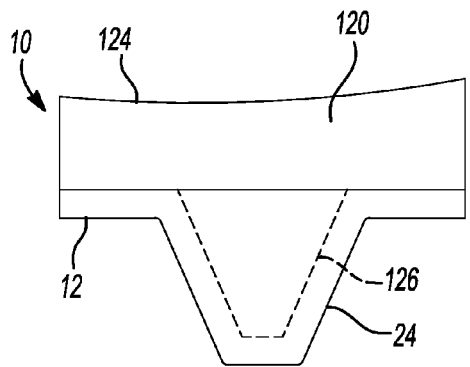
FIG. 6B illustrates the rotatable bearing mounted to a tibial baseplate according to the present teachings.

With additional reference to FIG. 6A, a rotatable bearing is illustrated at reference number 120. The rotatable bearing 120 includes a first coupling surface 122 and an articulation surface 124. The articulation surface 124 is configured to articulate with the femoral component 210, and the rotatable bearing 120 may be coupled to the medial tibial baseplate 12A or the lateral tibial baseplate 12B. For example and with reference to FIG. 6B, a generic tibial baseplate 12 including a second coupling surface 126 is illustrated. The tibial baseplate 12 represents either one of the tibial baseplates 12A or 12B. The second coupling surface 126 is defined by a generic bone anchor 24, which is configured to be secured within a tibia bone in any suitable manner, such as with bone cement. The second coupling surface 126 is configured to receive and couple the first coupling surface 122 thereto in any suitable manner, such as with a taper lock connection as illustrated. The first and second coupling surfaces 122 and 126 are configured to permit rotation of the rotatable bearing 120 with respect to the tibial baseplate 12 while keeping the rotatable bearing 120 secured to the tibial baseplate 12, and thus the first and second coupling surfaces 122 and 126 may be conical. Either one or both of the medial and lateral tibial baseplates 12A and 12B can include the rotatable bearing 120.

Figure 6C:
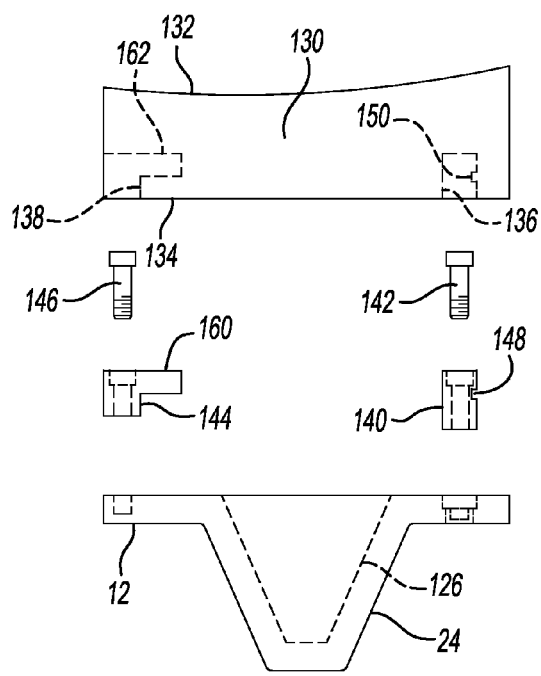
FIG. 6C is an exploded view of a fixed bearing according to the present teachings and the tibial baseplate of FIG. 6B.
Figure 6D:
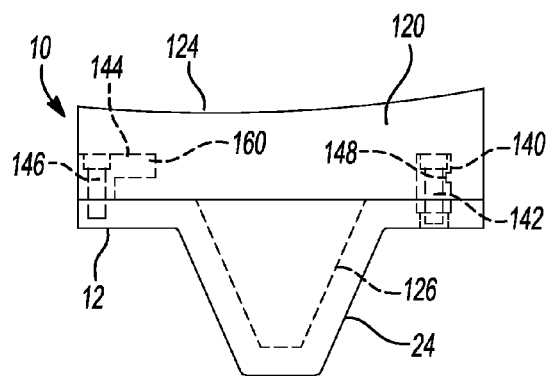
FIG. 6D illustrates the fixed bearing and the tibial baseplate of FIG. 6C coupled together.

With additional reference to FIGS. 6C and 6D, the tibial baseplate 12, which is generic to and represents either one of the medial or lateral baseplates 12A and 12B, can be modified to replace the rotatable bearing 120 with a fixed bearing 130. The fixed bearing 130 generally includes an articulation surface 132 and a tibial baseplate engaging surface 134 opposite thereto.

The tibial baseplate engaging surface 134 defines an anterior receptacle 136 and a posterior receptacle 138. The anterior receptacle 136 is sized and shaped to receive therein an anterior locking member 140 coupled to the tibial baseplate 12 with an anterior fastener 142. A posterior locking member 144 is secured to the tibial baseplate 12 with a posterior fastener 146.

The anterior and posterior locking members 140 and 144 can have any suitable feature to secure the fixed bearing 130 thereto in a fixed position. For example, the anterior locking member 140 can define a notch 148 keyed to receive flange 150 of the anterior receptacle therein in order to secure the interior locking member 140 within the anterior receptacle 136, and thus secure the fixed bearing to the tibial baseplate 12 in a fixed manner. The posterior locking member 144 can include a flange 160 sized and shaped to be securely received within a recess 162 defined within the posterior receptacle 138 in order to retain the posterior locking member 144 within the posterior receptacle 138, and fixedly secure the fixed bearing 130 to the tibial baseplate 12. Therefore, either one of the medial and lateral tibial baseplates 12A and 12B can be modified pursuant to the teachings of FIGS. 6A-6D to accommodate rotatable bearing 120 when the anterior and posterior locking members 140 and 144 are not in place, or to include the fixed bearing 130 fixed to one or both of the medial and lateral tibial baseplates 12A and 12B with one or both of the anterior and posterior locking members 140 and 144.

Figures 7A, 7B:
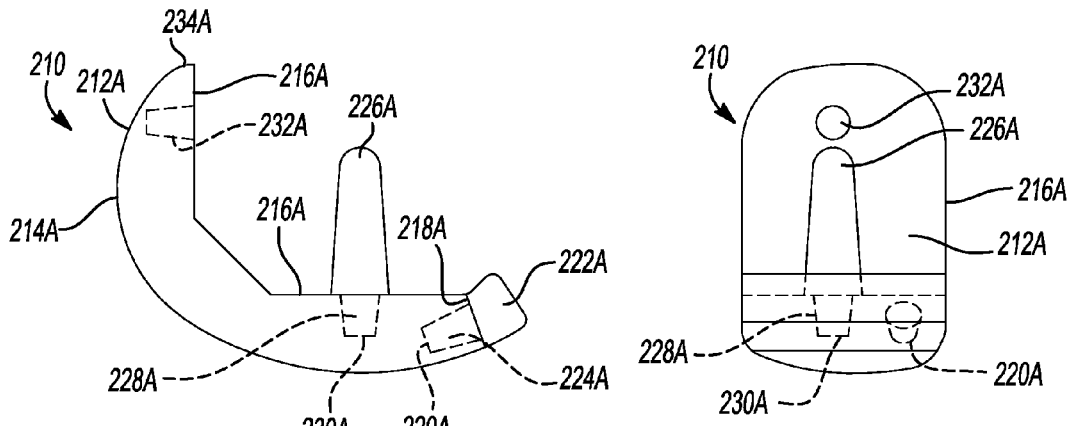
FIG. 7A is a side view of a first or medial condylar member of a femoral component according to the present teachings.
FIG. 7B is an anterior view of the first or medial condylar member of FIG. 7A.

FIGS. 7A-12 illustrate various members or portions of the universal femoral component 210 according to the present teachings. With reference to FIGS. 7A and 7B, a first or medial condylar member is illustrated at reference numeral 212A. The medial condylar member 212A generally includes an articulation surface 214A and a bone engaging surface 216A opposite thereto. The articulation surface 214A is configured to articulate with the medial bearing 40A coupled to the bearing engaging surface 14A of the medial tibial baseplate 12A.

At an anterior end 218A, the medial condylar member 212A includes a first medial coupling portion 220A. As illustrated, the first medial coupling portion 220A defines a tapered receptacle. However, the first medial coupling portion 220A can be any suitable coupling portion or member of any suitable size, shape, or configuration. As illustrated in FIGS. 7A and 7B, a cover 222A is mounted to the anterior end 218A through cooperation between a cover coupling portion 224A of the cover 222A and the first medial coupling portion 220A. The cover coupling portion 224A can be any suitable coupling portion or member configured to couple with the first medial coupling portion 220A. As illustrated, the cover coupling portion 224A is a tapered flange configured to be secured within the first medial coupling portion 220A with a taper lock.

The medial condylar member 212A further includes a modular stem 226A having a stem coupling portion 228A. The stem coupling portion 228A is configured to couple with a second medial coupling portion 230A at the bone engaging surface 216A. The coupling portions 228A and 230A can be any suitable coupling portions or members configured to secure the modular stem 226A to the medial condylar member 212A at the bone engaging surface 216A. As illustrated, the stem coupling portion 228A is a tapered flange and the second medial coupling portion 230A is a tapered receptacle, each of which are configured to provide a taper lock between the modular stem 226A and the medial condylar member 212A.

The medial condylar member 212A can further include a third medial coupling portion 232A at any suitable location of the bone engaging surface 216A, such as proximate to a posterior end 234A of the medial condylar member 212A as illustrated. The third medial coupling portion 232A is a tapered receptacle as illustrated, but can be any suitable coupling portion or coupling member configured to mount, for example, a modular box 250 (FIGS. 9-11) or a bone augment or body 260 (FIG. 12) as further described herein.

The medial condylar member 212A provides a partial or uni-femoral implant for resurfacing or replacing a damaged medial condyle of a femur. The modular stem 226A can be anchored within the femur in any suitable manner, such as with bone cement. The present teachings further provide for a second or lateral condylar member 212B (FIGS. 8B and 8C), which is substantially similar to or identical to the medial condylar member 212A. Therefore, the description of the medial condylar member 212A also applies to the lateral condylar member 212B and features of the lateral condylar member 212B in common with the medial condylar member 212A are illustrated with the same reference numbers, but with the suffix "B." One or both of the medial and lateral condylar members 212A and 212B can be implanted within the femur depending on the arthroplasty.

Figures 8A, 8B:
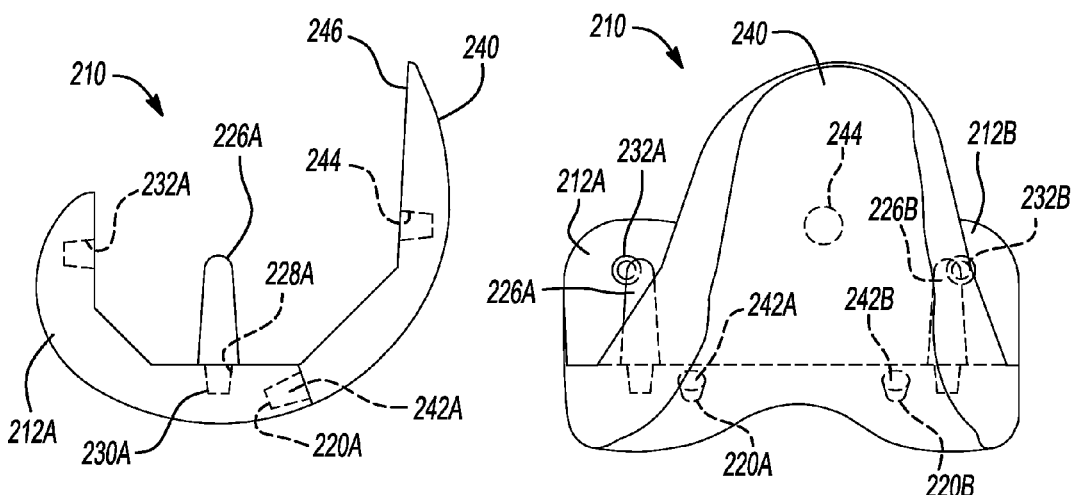
FIG. 8A is a side view of the first or medial condylar member of FIGS. 7A and 7B coupled to a patellar member of the femoral component.
FIG. 8B is an anterior view of the femoral component according to the present teachings including the first or medial condylar member coupled thereto, and a second or lateral condylar member coupled thereto.
Figure 8C:
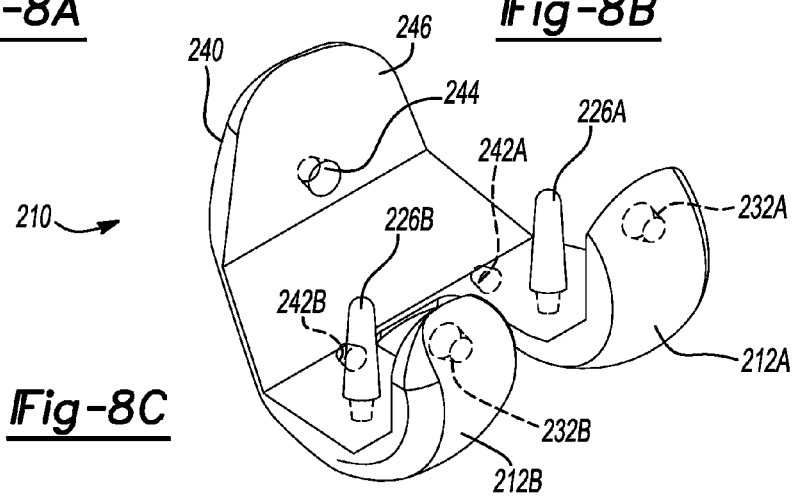
FIG. 8C is a perspective view of the femoral component of FIG. 8B.

With reference to FIGS. 8A-8C, depending on the arthroplasty the femoral component 210 can further include a patellar member 240, which can be implanted in the femur on its own, or coupled to one or both of the medial and lateral condylar members 212A and 212B. The patellar member 240 includes a medial patellar coupling portion 242A and a lateral patellar coupling portion 242B, which can be similar to or identical to the medial patellar coupling portion 242A. The medial and lateral patellar coupling portions 242A and 242B can each include a tapered flange as illustrated. The medial and lateral patellar coupling portions 242A and 242B can each be sized and shaped to be received within the medial and lateral coupling portions 220A and 220B respectively in order to secure the patellar member 240 to one or both of the medial and lateral condylar members 212A and 212B, such as with a taper lock.

Thus the patellar member 240 can be coupled to a femur with one or both of the medial and lateral condylar members 212A and 212B coupled thereto. Further, the patellar member 240 can be mounted to the femur with neither one of the medial and lateral condylar members 212A and 212B coupled thereto. Whether the patellar member 240 is coupled to one, both, or neither of the medial and lateral condylar members 212A and 212B will typically depend on the location of the damaged or diseased bone. For example, if the medial condyle of the femur is healthy, the medial condylar member 212A need not be implanted and thus need not be coupled to the patellar member 240. If the lateral condyle is healthy, the lateral condylar member 212B need not be coupled to the patellar member 240 or implanted. If only the portion of the femur proximate to the patella is damaged or diseased, then only the patellar member 240 need be implanted. With the medial and lateral condylar members 212A and 212B coupled to the patellar member 240, the femoral component 210 provides a cruciate retaining (CR) femoral component of the knee replacement system according to the present teachings.

The patellar member 240 can further include one or more patellar coupling portions 244. As illustrated, patellar coupling portion 244 is a tapered receptacle within a bone-engaging surface 246 of the patellar member 240. However, the patellar coupling portion 244 can have any other suitable size, shape or configuration, or can be any suitable coupling member, configured to couple with the modular box 250 or the body 260 described herein, for example.

Figure 9:
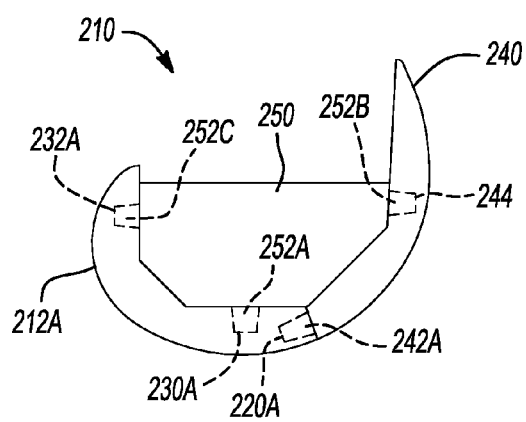
FIG. 9 is a side view of the femoral component according to the present teachings with a modular box coupled to a bone engaging surface of the femoral component.
Figure 10:
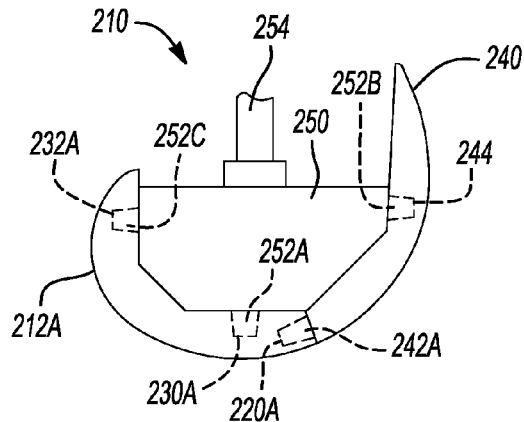
FIG. 10 is a side view of the femoral component according to the present teachings with the modular box including a stem.

With reference to FIGS. 9-11, the femoral component 210 can further selectively include, depending on the arthroplasty, the modular intercondylar box 250 coupled to the patellar member 240 and the medial and lateral condylar members 212A and 212B. The box 250 can be any suitable modular intercondylar box 250, such as an open or closed box. The modular intercondylar box 250 can provide the femoral component 210 as a posterior stabilized femoral component of the knee replacement system.

The modular intercondylar box 250 can be coupled to the patellar member 240 and the medial and lateral condylar members 212A and 212B in any suitable manner. For example, the modular intercondylar box 250 can include an intercondylar box coupling portion 252A configured to couple with the second medial coupling portion 230A, and another intercondylar box coupling portion (not shown) lateral to the coupling portion 252A configured to couple with the second lateral coupling portion 230B of the lateral condylar member 212B, such as with a taper lock. To further secure the modular intercondylar box 250 in place, it may further include a patellar box coupling portion 252B configured to couple with the patellar coupling portion 244, such as with a taper lock as illustrated. The modular intercondylar box 250 can still further include a medial box coupling portion 252C configured to couple with the third medial coupling portion 232A in any suitable manner, such as with a taper lock as illustrated. The modular intercondylar box 250 can include a lateral box coupling portion (not shown), which is similar to the medial box coupling portion 252C, that is configured to couple with the third lateral coupling portion 232B of the lateral condylar member 212B in order to secure the modular intercondylar box 250 to the lateral condylar member 212B.

With reference to FIG. 10, the modular intercondylar box 250 can include a stem 254, which can be implanted in the femur in any suitable manner, such as with bone cement. The stem 254 can be used with arthroplasties where additional stability of the femoral component 210 is appropriate, such as during a revision procedure. The stem 254 can be modular and coupled to the box 250 in any suitable manner. The stem 254 can also be integral or monolithic with the box 250.

With reference to FIG. 11, the modular intercondylar box 250 can define a receptacle 256 configured to receive the articulation portion 82 of the yoke 80 therein in order to couple the femoral component 210 and the tibial component 10 together with the yoke 80, which can provide a bone conserving hinge.

With reference to FIG. 12, the patellar member 240 and the medial and lateral condylar members 212A and 212B can be coupled to a bone augment body 260 for arthroplasties in which a large amount of bone needs to be replaced, such as for salvage arthroplasties in which a segmental implant is used. Extending from the bone augment body 260 is a stem 262. The stem 262 can be modular or integral with the body 260.

The body 260 can include a distal coupling portion 266A configured to couple with the second medial coupling portion 230A of the medial condylar member 212A, such as with a taper lock as illustrated. The body 260 can also include a similar coupling portion (not shown) configured to couple with the second lateral coupling portion 230B of the lateral condylar member 212B. A patellar coupling portion 266B of the body 260 can couple with the patellar coupling portion 244 of the patellar member 240 in order to secure the body to the patellar member 240, such as with a taper lock as illustrated. The body 260 can further include a medial coupling portion 266C configured to couple with the third medial coupling portion 232A of the medial condylar member 212A in order to secure the body 260 to the medial condylar member 212A. The body 260 can also include a lateral coupling portion (not shown) similar to the medial coupling portion 266C, which is configured to couple to the third lateral coupling portion 232B of the lateral condylar member 212B in order to secure the body 260 to the lateral condylar member 212B.

Figure 13A:
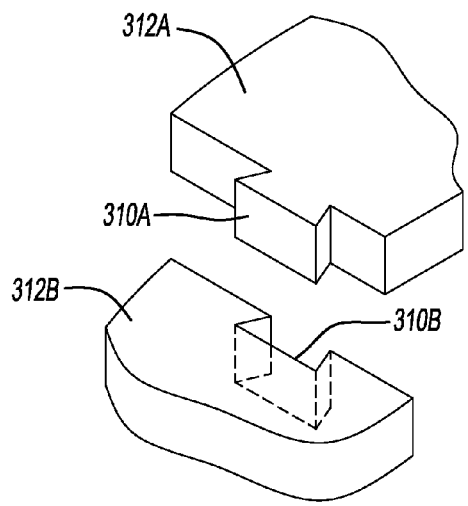
FIGS. 13A, 13B, 13C, 13D, and 13E illustrate additional coupling portions according to the present teachings for the tibial and femoral components.

The coupling portions described throughout the present teachings can be any suitable coupling portions or members configured to couple two portions of the tibial component 10 together, or two portions of the femoral component 210 together, in addition to the taper lock coupling portions described above. For example, FIG. 13A illustrates additional coupling portions according to the present teachings, which can be substituted for any of the other coupling portions described herein. Specifically, FIG. 13A illustrates a dovetail flange 310A of a first member 312A and a dovetail receptacle 310B of a second member 312B. The dovetail receptacle 310B is configured to receive the dovetail flange 310A in order to secure the first and second members 312A and 312B together. The first and second members 312A and 312B are generic members representing any two members of the tibial component 10 configured to be coupled together as described above, or any two members of the femoral component 210 configured to be coupled together as described above.

Figure 13B:
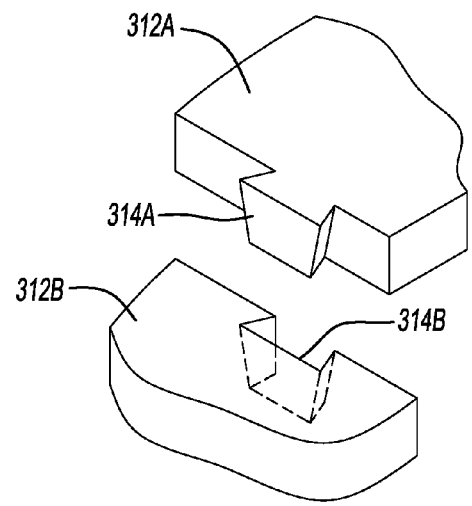

FIG. 13B illustrates additional coupling portions in the form of a tapered dovetail flange 314A configured for receipt within a tapered dovetail receptacle 314B in order to secure the first and second members 312A and 312B together.

Figure 13C:
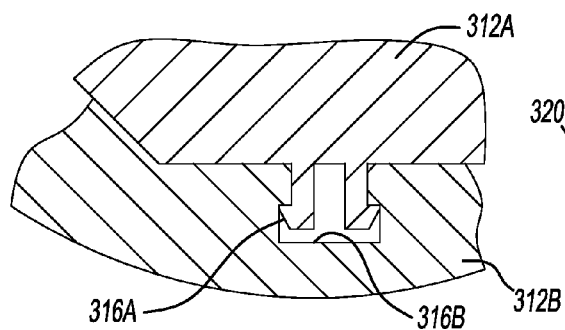

With reference to FIG. 13C, any of the coupling portions described herein can take the form of flexible fingers 316A configured for receipt within receptacles 316B, such as through snap fit cooperation between the flexible fingers 316A and the receptacles 316B.

Figure 13D:
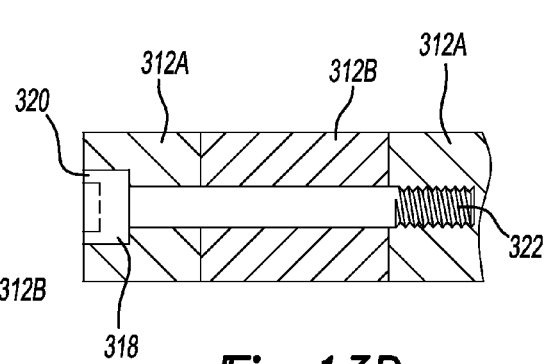

FIG. 13D illustrates a fastener 318 including a head 320 and threads 322 at a distal end thereof. Any of the coupling members described herein can be configured to include, or be replaced by, the fastener 318 to secure any two members 312A and 312B together in any suitable manner.

Figure 13E:
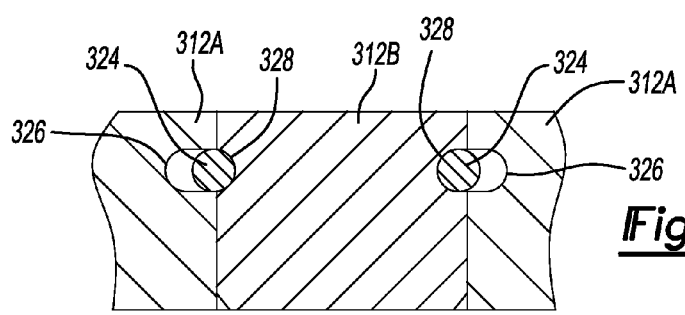

With reference to FIG. 13E, a flexible retention member 324, such as a flexible ring, can be included with, or replaced by, any of the coupling portions described in the present teachings. For example, the flexible retention member 324 can be seated within a receptacle 326 of the first member 312A such that upon engagement of the second member 312B with the first member 312A the flexible retention member 324 extends into recess 328, such as an annular recess, of the second member 312B in order to couple the first and second members 312A and 312B together.

The present teachings thus provide a knee replacement system including a tibial component 10 that can selectively include, depending on the type of arthroplasty, one or more of at least the following: the medial tibial baseplate 12A only; the lateral tibial baseplate 12B only; the medial and lateral tibial baseplates 12A and 12B coupled together with the intercondylar bridge member 50 without the insert 60 mounted to the medial and lateral tibial baseplates 12A and 12B in the space 54 defined therebetween; the medial and lateral tibial baseplates 12A and 12B coupled together with the bridge member 50 and the insert 60 coupled to the medial and lateral tibial baseplates 12A and 12B in the space 54, the insert 60 including the stem 68 or the elongated stem 70, and the stem 68 with or without the yoke 80; the tibial component 10 with or without the augment 90 coupled to the insert 60; the tibial component 10 with or without the augment 102 coupled to the medial and lateral tibial baseplates 12A and 12B in the space 54; a rotatable bearing 120 coupled to one or both of the medial and lateral tibial baseplates 12A or 12B; or the fixed bearing 130 coupled to the medial or lateral tibial baseplates 12A or 12B.

The present teachings further provide for a femoral component 210 that can selectively include, depending on the type of arthroplasty, one or more of at least the following: the medial condylar member 212A only; the lateral condylar member 212B only; the patellar member 240 only; the patellar member 240 coupled to one or both of the medial and lateral condylar members 212A and 212B; the medial and lateral condylar members 212A and 212B with or without the modular stem 226A; the modular box 250, which may or may not include a stem 254 and may or may not include the receptacle 256 for the yoke 80; and the bone augment body 260.

The present teachings thus provide a knee replacement system including a plurality of modular femoral and modular tibial components, which can be selectively coupled together depending upon the requirements of the particular arthroplasty being performed. With respect to revision procedures, for example, portions of the tibial component 10 or the femoral component 210 not yet implanted can be coupled to members that were implanted previously. For example, with respect to the tibial component 10, if only the medial tibial baseplate 12A was previously implanted, the lateral tibial baseplate 12B may be implanted and coupled to the medial tibial baseplate 12A with the bridge member 50 during a revision procedure. With respect to the femoral component 210, for example, if the patellar member 240 with only the medial condylar member 212A coupled thereto was previously implanted, the lateral condylar member 212B may be coupled to the patellar member 240 at the lateral patellar coupling portion 242B thereof during a revision procedure such that the implanted femoral component has both the medial and lateral condylar members 212A and 212B. Applicant's tibial and femoral components 10 and 210 thus provide numerous advantages, such as the ability to selectively couple together various implant components depending on the required arthroplasty without the need for separate tibial and/or femoral components to provide all of the different combinations described herein, which conserves resources and costs.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A modular knee replacement system comprising:
a medial tibial baseplate, a lateral tibial baseplate separate and distinct from the medial tibial baseplate, a plate-shaped intercondylar bridge member separate and distinct from the medial tibial baseplate and the lateral tibial baseplate, and a plate-shaped insert, the insert being separate and distinct from the intercondylar bridge member, the insert including a stem, each one of the medial and lateral tibial baseplates including:
a bone engaging surface and a bearing engaging surface opposite to the bone engaging surface, wherein the bone engaging surface of each of the medial and lateral tibial baseplates includes a bone anchor extending from the bone engaging surface, the bearing engaging surfaces configured to couple with tibial bearings; and
an anterior baseplate coupling portion located on an inner side surface of the medial and the lateral tibial baseplates, and a posterior baseplate coupling portion located on the same inner side surface of each of the medial and the lateral tibial baseplates, the anterior baseplate coupling portion configured to couple with the intercondylar bridge member on opposing side surfaces of the intercondylar bridge member for coupling the medial tibial baseplate to the lateral tibial baseplate, the posterior baseplate coupling portion configured to fasten the insert to each of the medial tibial baseplate and the lateral tibial baseplate on opposing side surfaces of the insert,
wherein the intercondylar bridge member is configured to couple the medial and the lateral baseplates together such that the medial and the lateral baseplates define a posteriorly-located space therebetween, the insert configured to be located within said space, wherein the intercondylar bridge member includes a first bridge coupling portion configured to couple with the anterior baseplate coupling portion of the medial tibial baseplate, and a second bridge coupling portion configured to couple with the anterior baseplate coupling portion of the lateral tibial baseplate, wherein the insert includes a first insert coupling portion configured to couple with the posterior baseplate coupling portion of the medial tibial baseplate, and a second insert coupling portion configured to couple with the posterior baseplate coupling portion of the lateral tibial baseplate, the first and second insert coupling portions configured to secure the insert to the medial and lateral tibial baseplates in the posteriorly-located space therebetween, wherein the coupling portions are selected from the group consisting of tapered coupling portions, dovetail coupling portions, coupling flanges, flexible fingers, and fasteners, and wherein the medial tibial baseplate, the lateral tibial baseplate, the intercondylar bridge member, and the insert are coplanar.

2. The knee replacement system of claim 1, wherein the insert defines a receptacle configured to receive a yoke therein.

3. The knee replacement system of claim 1, further comprising a bone augment configured to couple with the insert proximate to a bone engaging surface of the insert.

4. The knee replacement system of claim 3, wherein the bone augment defines a tapered coupling surface configured to couple the bone augment to the stem of the insert.

5. The knee replacement system of claim 4, wherein the bone augment includes a first wing and a second wing extending from a hub defining the tapered coupling surface of the augment.

6. The knee replacement system of claim 1, wherein the bearing engaging surface is configured to independently couple with both a fixed bearing and a rotatable bearing.

7. The knee replacement system of claim 1, further comprising a femoral component including at least one of the following:
 a medial condylar member including a first coupling portion configured to couple with a patellar member;
 a lateral condylar member including a second coupling portion configured to couple with the patellar member;
 or the patellar member including a medial coupling portion configured to couple with the first coupling portion and a lateral coupling portion configured to couple with the second coupling portion.

8. The knee replacement system of claim 7, wherein each one of the medial and lateral condylar members are configured to individually couple with a stem, an intercondylar box, or a bone augment.

* * * * *